United States Patent
Pansare et al.

(10) Patent No.: US 8,815,962 B2
(45) Date of Patent: Aug. 26, 2014

(54) LOW TEMPERATURE SULFUR TOLERANT TAR REMOVAL WITH CONCOMITANT SYNTHESIS GAS CONDITIONING

(75) Inventors: Sourabh S. Pansare, Bartlesville, OK (US); Joe D. Allison, Bartlesville, OK (US); Steven E. Lusk, Ponca City, TX (US); Albert C. Tsang, Sugar Land, TX (US)

(73) Assignee: Lummus Technology Inc., Bloomfield, NJ (US)

( * ) Notice: Subject to any disclaimer, the term of this patent is extended or adjusted under 35 U.S.C. 154(b) by 0 days.

(21) Appl. No.: 13/811,161

(22) PCT Filed: Sep. 13, 2011

(86) PCT No.: PCT/US2011/051460
§ 371 (c)(1),
(2), (4) Date: Jan. 18, 2013

(87) PCT Pub. No.: WO2012/037164
PCT Pub. Date: Mar. 22, 2012

(65) Prior Publication Data
US 2013/0116345 A1    May 9, 2013

Related U.S. Application Data

(60) Provisional application No. 61/382,140, filed on Sep. 13, 2010.

(51) Int. Cl.
*C07C 27/00*    (2006.01)

(52) U.S. Cl.
USPC .................... 518/702; 518/700; 518/715

(58) Field of Classification Search
USPC ............................ 518/700, 702, 715
See application file for complete search history.

(56) References Cited

U.S. PATENT DOCUMENTS

| | | |
|---|---|---|
| 3,928,000 A | 12/1975 | Child et al. |
| 5,230,789 A | 7/1993 | Chao et al. |
| 2007/0299288 A1 | 12/2007 | Seemann et al. |
| 2010/0096594 A1 | 4/2010 | Dahlin et al. |
| 2010/0205863 A1 | 8/2010 | Biollaz et al. |

*Primary Examiner* — Jafar Parsa
(74) *Attorney, Agent, or Firm* — Osha • Liang LLP

(57) ABSTRACT

A catalyst comprising NiO, a metal mixture comprising at least one of MoO3 or WO3, a mixture comprising at least one of $SiO_2$ and $Al_2O_3$, and $P_2O_5$. In this embodiment the metal sites on the catalyst are sulfided and the catalyst is capable of removing tar from a synthesis gas while performing methanation and water gas shift reactions at a temperature range from 300° C. to 600° C.

11 Claims, 6 Drawing Sheets

LOW TEMPERATURE SULFUR TOLERANT TAR REMOVAL WITH CONCOMITANT SYNTHESIS GAS CONDITIONING

CROSS-REFERENCE TO RELATED APPLICATIONS

This application is a non-provisional application which claims the benefit of and priority to U.S. Provisional Application Ser. No. 61/382,140 filed Sep. 13, 2010, entitled "Low Temperature Sulfur Tolerant Tar Removal with Concomitant Synthesis Gas Conditioning," which is hereby incorporated by reference in its entirety.

STATEMENT REGARDING FEDERALLY SPONSORED RESEARCH OR DEVELOPMENT

None.

FIELD OF THE INVENTION

A low temperature sulfur tolerant tar removal catalyst.

BACKGROUND OF THE INVENTION

Synthesis gas has various impurities such as tars, $H_2S$, $NH_3$ and particulates. Tars, commonly defined as polynuclear aromatic compounds formed in the pyrolysis of carbonaceous materials such as wood, coal, or peat, are responsible for operational problems such as plugging of process lines and fouling of heat exchange surfaces which results in reduced process efficiency and plant shutdowns. Tars have the propensity to act as coke precursors resulting in catalyst deactivation downstream of the gasifier. Additionally some components of tars are known carcinogens. Hence, it is important to remove tars from synthesis gas streams for the economical conversion of synthesis gas to value added products.

The concentrations of tars can vary depending upon feedstocks, gasifier type and operating conditions. Most downstream conversion processes and equipments have zero or very low (in ppb range) tolerance for tars. Although catalytic removal of tars is the simplest and the most economical method, there are no commercialized low temperature (<500° C.) tar removal catalysts even after continued 25 years of research and development efforts. Catalysts currently used in the art require temperatures of at least 600° C. preferably 800° C. which requires heating and expensive equipment. By taking the synthesis gas straight out of the generator absent any additional heating additional costs and machinery are not required.

There exists a need to find a tar removal catalyst that exhibits: 1) sulfur tolerance; 2) resistance to coking; 3) ability to withstand high temperatures and reducing environment; 4) ability to work in the presence of $NH_3$, HCl and some heavy metals; and 5) attrition resistance.

BRIEF SUMMARY OF THE DISCLOSURE

A catalyst comprising NiO, a metal mixture comprising or comprising essentially of at least one of MoO3 or WO3, a mixture comprising at least one of $SiO_2$ and Al2O3, and P2O5. In this embodiment the metal sites on the catalyst are sulfided and the catalyst is capable of removing tar from a synthesis gas while performing methanation and water gas shift reactions at a temperature range from 300° C. to 600° C.

In an alternate embodiment a catalyst comprising or comprising essentially of a NiO present from 1 to 10 wt %, a metal mixture comprising of $MoO_3$ from 10 to 20 wt %, a mixture comprising at least one of: $SiO_2$ and $Al_2O_3$ and $P_2O_5$ from 0.001 to 1 wt %. In this embodiment the metal sites on the catalyst are sulfided and the catalyst is capable of removing tar while performing a methanation reaction and a water gas shift reaction simultaneously from an unheated synthesis gas. The catalyst is capable of removing tar with greater than 65% conversion at 350° C., performing a methanation reaction, producing from 150 to 800 µmol/g cat/s of $CH_4$ and a water gas shift reaction, producing from 30 to 50% CO conversion, at a temperature range from 350° C. to 550° C.

In another embodiment the process begins by producing a synthesis gas. The synthesis gas is then contacted with a catalyst to produce a treated synthesis gas. In this embodiment the catalyst comprises or comprising essentially of NiO, a metal mixture comprising at least one of MoO3 or WO3, a mixture comprising at least one of SiO2 and Al2O3, and P2O5. The metal sites on the catalyst are sulfided and the catalyst is capable of removing tar from a synthesis gas while performing methanation and water gas shift reactions at a temperature range from 300° C. to 600° C. The treated synthesis gas is then introduced to a catalytic chemical reaction. In this embodiment the synthesis gas is not heated prior to contact with the catalyst and the treated synthesis gas is not cooled prior to undergoing the catalytic chemical reaction.

In yet another embodiment the process begins by producing a synthesis gas. The synthesis gas is then contacted with a catalyst to produce a treated synthesis gas. In this embodiment the catalyst comprises or comprising essentially of NiO present from 1 to 10 wt %, a metal mixture comprising of $MoO_3$ from 10 to 20 wt %, a mixture comprising at least one of: $SiO_2$ and $Al_2O_3$ and $P_2O_5$ from 0.001 to 1 wt %. In this embodiment the metal sites on the catalyst are sulfided and the catalyst is capable of removing tar while performing a methanation reaction and a water gas shift reaction simultaneously from an unheated synthesis gas. The catalyst is capable of removing tar with greater than 65% conversion at 350° C., performing a methanation reaction, producing from 150 to 800 µmol/g cat/s of $CH_4$ and a water gas shift reaction, producing from 30 to 50% CO conversion, at a temperature range from 350° C. to 550°. The treated synthesis gas is then introduced to a catalytic chemical reaction. In this embodiment the synthesis gas is not heated prior to contact with the catalyst and the treated synthesis gas is not cooled prior to undergoing the catalytic chemical reaction.

BRIEF DESCRIPTION OF THE DRAWINGS

A more complete understanding of the present invention and benefits thereof may be acquired by referring to the follow description taken in conjunction with the accompanying drawings in which.

DETAILED DESCRIPTION

Figure 1:
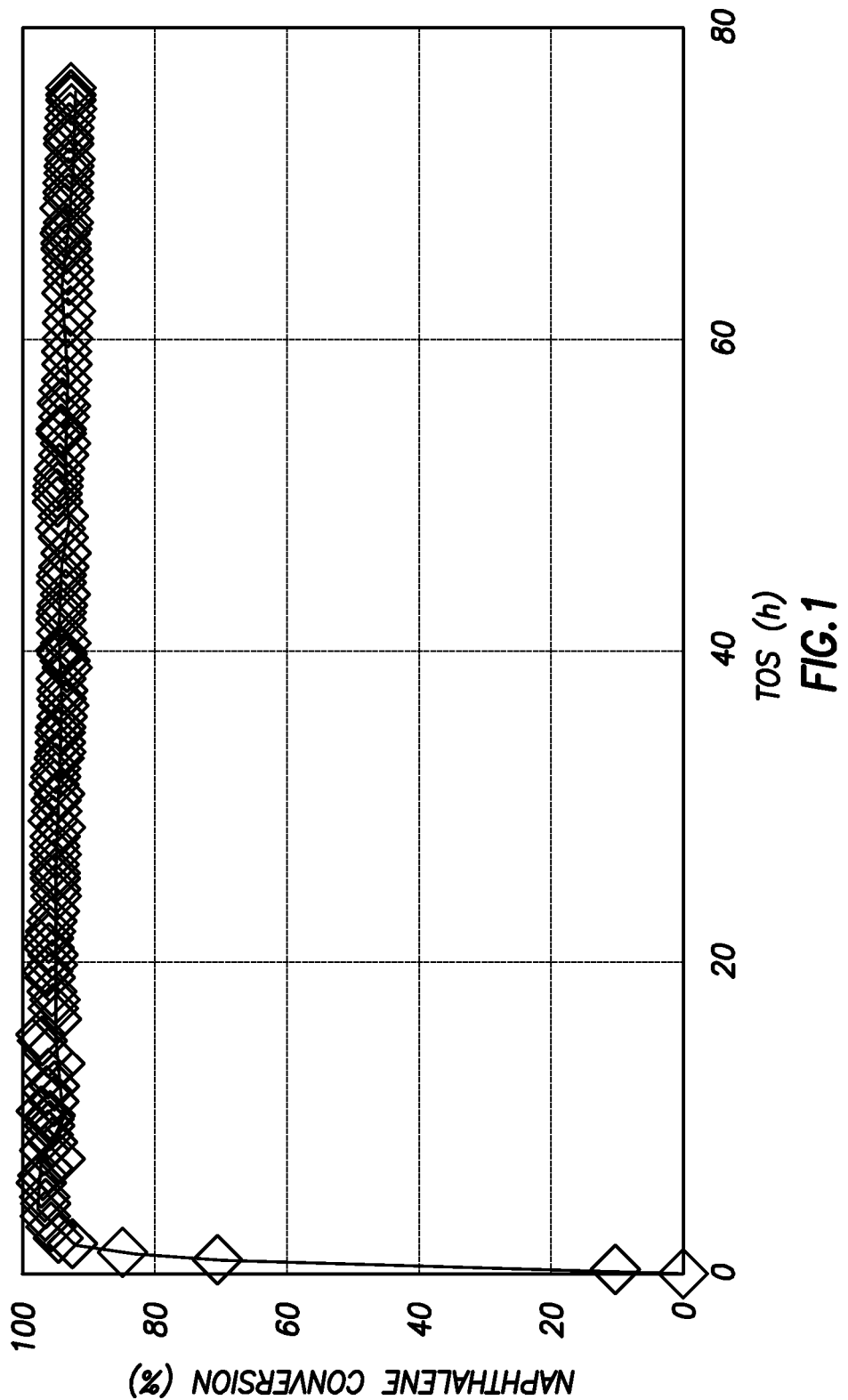
FIG. 1 depicts the performance of the catalyst at 500 psig, 5.5 h$^{-1}$ and 350° C.

Turning now to the detailed description of the preferred arrangement or arrangements of the present invention, it should be understood that the inventive features and concepts may be manifested in other arrangements and that the scope of the invention is not limited to the embodiments described or illustrated. The scope of the invention is intended only to be limited by the scope of the claims that follow.

In one embodiment the catalyst comprises NiO, a metal mixture comprising at least one of $MoO_3$ or $WO_3$, a mixture comprising at least one of $SiO_2$ and $Al_2O_3$, and $P_2O_5$. In this embodiment the metal sites on the catalyst are sulfided and the catalyst is capable of removing tar from a synthesis gas while performing methanation and water gas shift reactions at a temperature range from 300° C. to 600° C.

In one embodiment the sulfided metal site describes metal with sulfur associated with it to give activity to the site. Sulfidation is typically achieved by using a sulfur molecule such a dimethyl disulfide, dimethyl sulfide or $H_2S$ gas to react with the metal oxide to form a metal sulfide.

In one embodiment the NiO is present from 0.5 to 15 wt %, 1 to 10 wt % or even 7.5 to 12.5 wt %. Alternatively other variations of Ni-based catalysts can be used as well, such as $NiS_2$. The Ni-based catalysts are additionally capable of water gas shift activity, is a chemical reaction in which carbon monoxide reacts with water vapor to form carbon dioxide and hydrogen ($CO+H_2O \rightarrow CO_2+H_2$). The additional $H_2$ produced is useful in methanation reactions ($3H_2+CO \rightarrow CH_4+H_2O$) that occur to produce additional water for the reactants of the water gas shift. Furthermore, the $H_2$ produced is also useful for the breakdown of naphthalene present in the tar ($mC_{10}H_8 + nH_2 \rightarrow CH_4+C_2H_6+C_3H_8+C_6H_6+coke$).

The methanation reaction can produce from 150 to 800 μmol/g cat/s of $CH_4$ formation, or even 300 to 700 μmol/g cat/s.

The water gas shift reaction can produce more than 30% CO conversion. In an alternate embodiment the water gas shift reaction can produce from 30-50% CO conversion.

In another embodiment the metal mixture comprising at least one of $MoO_3$ or $WO_3$ is present from 5 to 25 wt %, 10 to 20 wt % or even 12.5 to 17.5 wt %. Alternatively other variations of Ni-based catalysts can be used as well, such as NiS.

In yet another embodiment the $P_2O_5$ is present from 0.001 to 1 wt %.

In one other embodiment the mixture comprising at least one of $SiO_2$ and $Al_2O_3$ is present from 59 to 95 wt %, 69% to 89 wt %.

In one embodiment the synthesis gas is not heated prior to contacting with the catalyst. By taking the synthesis gas straight out of the generator any additional heating costs and machinery are not required. Furthermore by contacting the synthesis gas with the catalyst at a temperature range from 300° C. to 600° C. the treated synthesis gas, after removal of sulfur and other impurities, would not need to be cooled prior to being utilized in a syngas conversion reactions such as Fischer-Tropsch and methanation.

The reaction between the catalyst and the synthesis gas can occur at pressure levels ranging from 14.7 to 1,500 psig, 14.7 to 1,200 psig or even 250 to 1,000 psig.

In one embodiment the temperature range for the reactions occur from 350° C. to 550° C. At a temperature of 350° C. the removal of tar has a conversion rate of greater than 65%. At a temperature of 400° C. the removal of tar has a conversion rate of greater than 70%.

In an alternate embodiment the catalyst comprises from 1-10 wt % NiO, a metal mixture comprising from 10-20 wt % of $MoO_3$, a mixture comprising at least one of $SiO_2$ and $Al_2O_3$, and from 0.001 to 1 wt % $P_2O_5$. In this embodiment the metal sites on the catalyst are sulfided. The catalyst is capable of removing tar from a synthesis gas with greater than 65% conversion at 350° C. Simultaneously the catalyst is also capable of performing a methanation reaction, producing from 150 to 800 μmol/g cat/s of $CH_4$, and a water gas shift reaction, producing from 30 to 50% CO conversion, at a temperature range from 300° C. to 600° C.

In yet another embodiment the process discloses producing a synthesis gas followed by producing a treated synthesis gas by contacting the synthesis gas with a catalyst. In this embodiment the catalyst can comprise NiO, a metal mixture comprising at least one of $MoO_3$ or $WO_3$, a mixture comprising at least one of $SiO_2$ and $Al_2O_3$, and $P_2O_5$. The treated synthesis gas is then introduced into a catalytic chemical reaction. In this embodiment the synthesis gas is not heated prior to contact with the catalyst and the treated synthesis gas is not cooled prior to undergoing the catalytic chemical reaction.

The catalytic chemical reaction can include reactions such as a Fischer Tropsch reaction, a methanation reaction or syngas to dimethyl ether to gasoline reaction. The Fischer-Tropsch reaction can be used to produce liquid fuels. Other catalytic reactions can be used to produce synthetic natural gas, alcohols, ammonia, gasoline or other chemical products.

By not heating the synthesis gas prior to contact with the catalyst additional heating sources are not required. Furthermore additional cooling of the treated synthesis gas is not required prior to the treated synthesis gas undergoing a catalytic chemical reaction, such as Fischer-Tropsch.

In one embodiment the synthesis gas contain more than, 1,000 ppmv of sulfur even more than 10,000 ppmv or even 15,000 ppmv of sulfur. In one example the amount of sulfur from the synthesis gas can range from 10,000 to 20,000 ppmv.

In another embodiment the process discloses producing a synthesis gas followed by producing a treated synthesis gas by contacting the synthesis gas with a catalyst. In this embodiment the catalyst can comprise from 1-10 wt % NiO, a metal mixture comprising from 10-20 wt % of $MoO_3$, a mixture comprising at least one of $SiO_2$ and $Al_2O_3$, and from 0.001 to 1 wt % $P_2O_5$. In this catalyst the metal sites are sulfided. Additionally, the catalyst is capable of removing tar from a synthesis gas with greater than 65% conversion at 350° C. Simultaneously the catalyst is also capable of performing a methanation reaction, producing from 150 to 800 μmol/g cat/s, and a water gas shift reaction, producing from 30 to 50% CO conversion, at a temperature range from 300° C. to 600° C. The treated synthesis gas is then introduced into a catalytic chemical reaction. In this embodiment the synthesis gas is not heated prior to contact with the catalyst and the treated synthesis gas is not cooled prior to undergoing the catalytic chemical reaction.

The following examples of certain embodiments of the invention are given. Each example is provided by way of explanation of the invention, one of many embodiments of the invention, and the following examples should not be read to limit, or define, the scope of the invention.

Example 1

In this example a NiMo catalyst was produced by calcining at 650° C. for 4 hours prior to use. The NiMo catalyst contains 4.0% NiO, 14.3% $MoO_3$, 81.7% $Al_2O_3$ with a surface area of 323.3 $m^2/g$.

Synthesis gas was flowed in at a pressure of 15 psig and at a reactor temperature range of 250-650° C. At this rate the following reaction occurred: $mC_{11}H_{10}+nH_2 \rightarrow CH_4+C_2H_6+C_3H_8+C_6H_6+coke$.

The removal of tar at 350° C. and 3000 h⁻¹ was 65%, while the removal of tar at 400° C. and 3000 h⁻¹ was 70%.

Example 2

A catalyst was evaluated comprising of 1-10 wt % NiO, 10-20 wt % MoO$_2$, a mixture comprising at least one of: SiO$_2$ and Al$_2$O$_3$ and less than 1 wt % of P$_2$O$_5$. The inlet stream of synthesis gas consisted of 28.5% H$_2$, 42% CO, 12% CO$_2$, 16% H$_2$O, 1.5% H$_2$S (equivalent to 15,000 ppmv of H$_2$S) and 200 ppmv of naphthalene. The reaction conditions for this reaction were 500 psig and a temperature range of 350 to 400° C. The catalyst was pre-sulfided in the presence of 5% H$_2$S/H$_2$ at 200° C. and 360 psig for 2 hours.

FIG. 1 demonstrates the performance of the catalyst at 500 psig, 5.5 h⁻¹ and 350° C. Methane, ethane, propane, iso-butane, iso-butylene, benzene, toluene, and xylene were the products of the naphthalene decomposition reaction.

Figure 2:
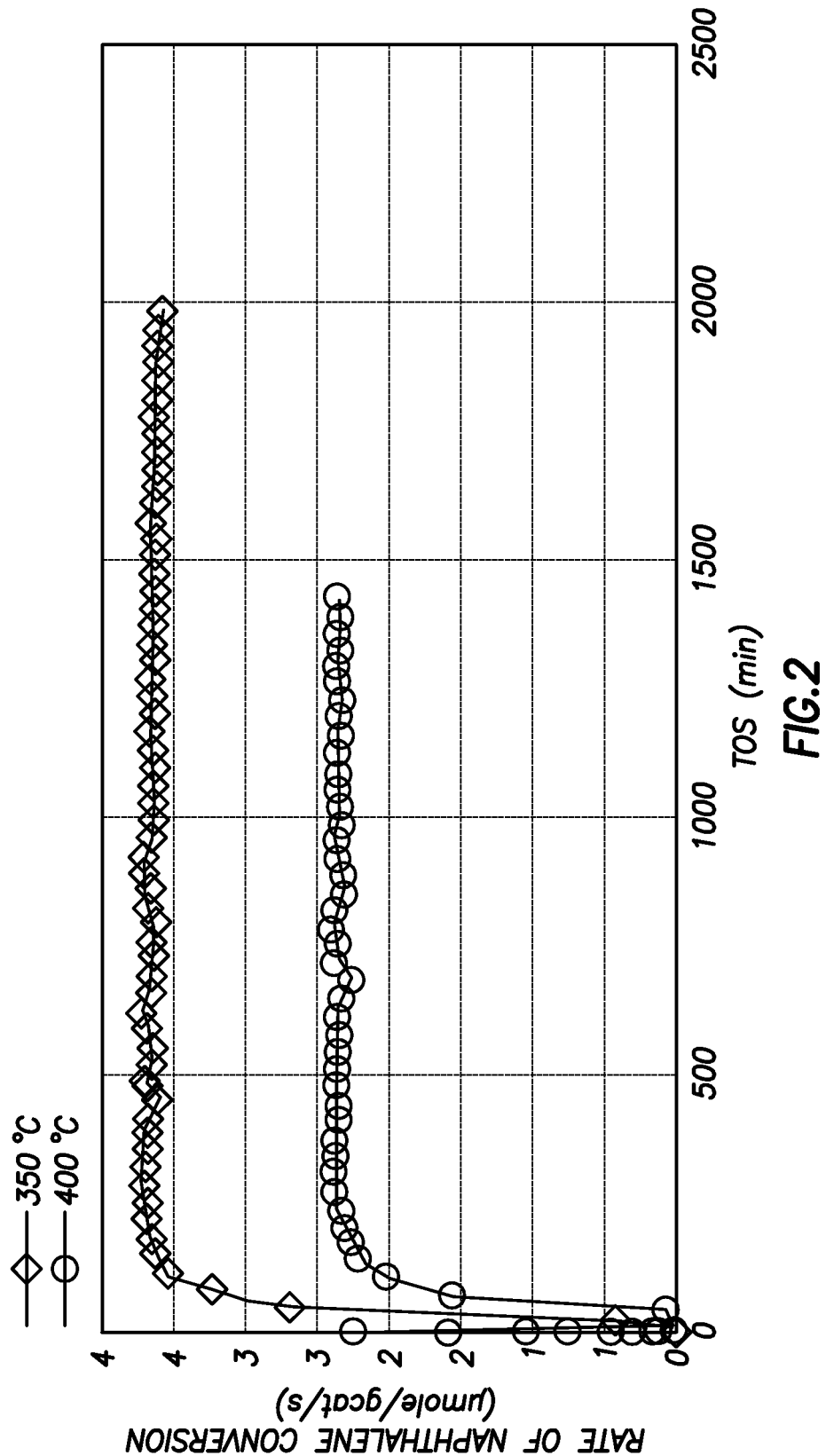
FIG. 2 depicts the rates of naphthalene conversion at 500 psig and 5.5 h$^{-1}$ at two different temperature rates of 350° C. and 400° C.

FIG. 2 demonstrates the naphthalene conversion at 500 psig and 5.5 h⁻¹ at two different temperature rates of 350° C. and 400° C. The average conversion rate of the naphthalene at 350° C. is 91% while the average conversion rate of the naphthalene at 400° C. is 100%.

It is theorized that the rate of naphthalene conversion at 350° C. is higher than that of 400° C. due to differences in the inlet naphthalene concentration. The inlet naphthalene concentration was much higher at 350° C. (228 ppmv) that at 400° C. (158 ppmv). This results in a higher rate of reaction at 350° C. as observed. If normalized for naphthalene concentration, the rate at 400° C. will be higher than that at 350° C.

Example 3

Different catalysts were tested to evaluate their ability for tar cracking, methanation, water gas shift and sulfur removal at low temperatures. In the following tables WHSV means weight hourly space velocity.

Five different catalysts were tested

| Catalyst | Types of sites | Form of metal sites |
| --- | --- | --- |
| Silica-alumina | Acidic sites | — |
| Tungstated zirconia | Acidic sites, some metal | Reduced metal/oxide |
| Ultra-stable Y zeolite | Acidic sites | — |
| NiW/zeolitic support | Metal and acid sites | Sulfide |
| NiMo/zeolitic support | Metal and acid sites | Sulfide |

Figure 3:
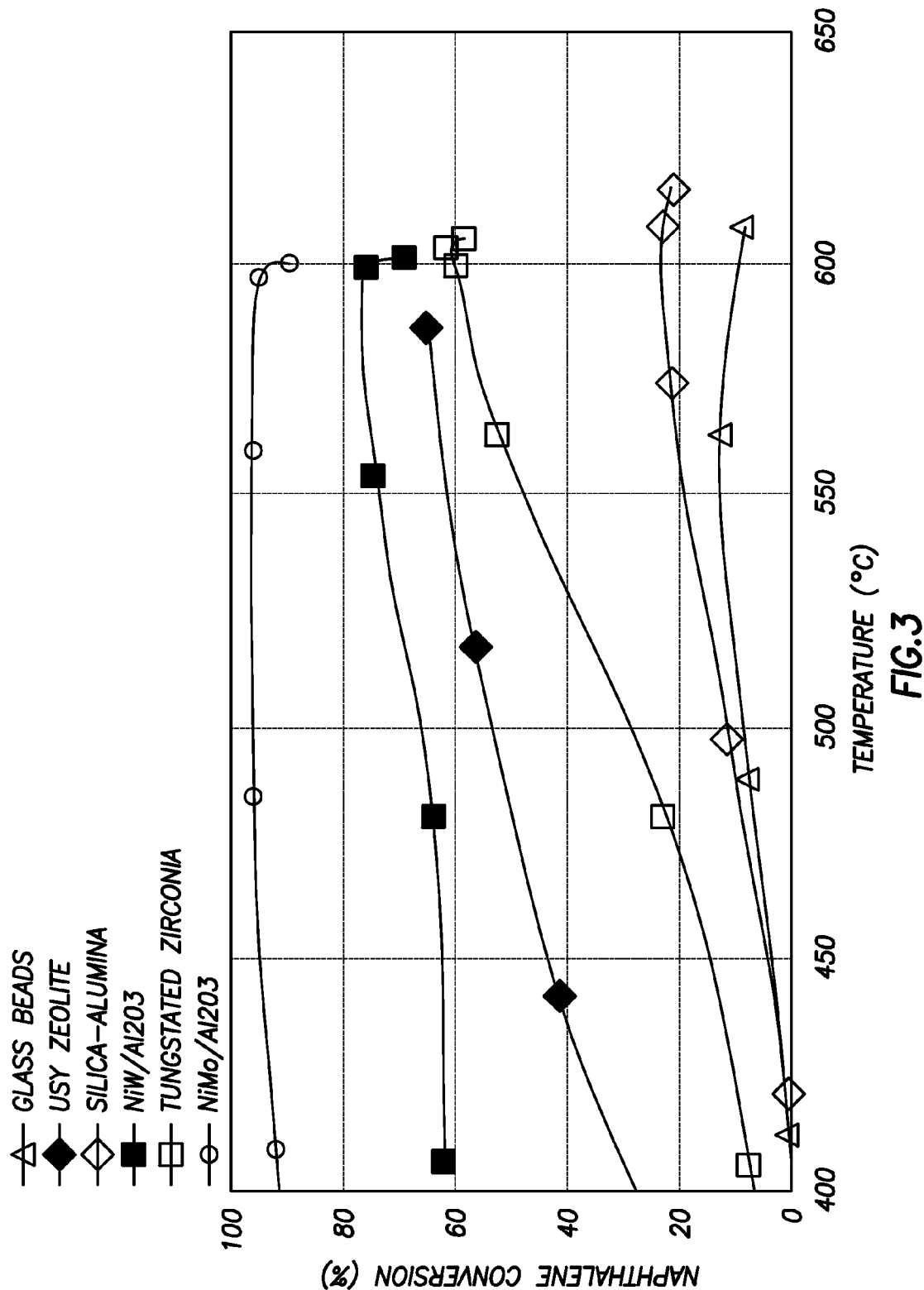
FIG. 3 depicts the naphthalene conversion at specified temperature ranges.
Figure 4:
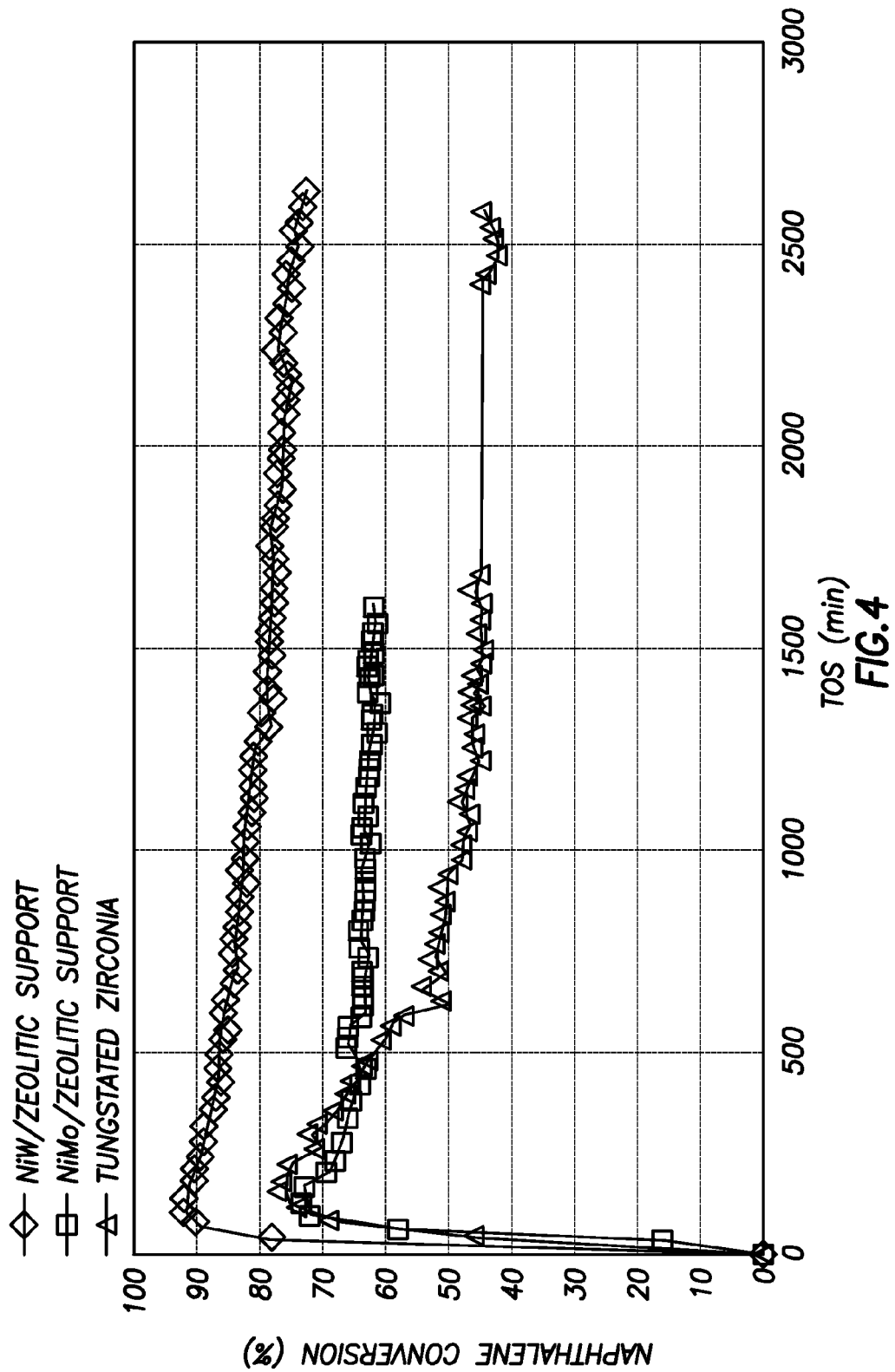
FIG. 4 depicts the naphthalene conversion for a specified period of time.

The ability for the catalysts to perform tar cracking is shown below and in FIG. 3 and FIG. 4. FIG. 3 demonstrates the naphthalene conversion at specified temperature ranges. FIG. 4 demonstrates the naphthalene conversion for a specified period of time.

| Catalyst | Temp. range ° C. | Pressure psig | WHSV h-1 | Naphthalene Conversion % |
| --- | --- | --- | --- | --- |
| Silica-alumina | 400-600 | 500 | 11 | <20% |
| Tungstated zirconia | 400-600 | 500 | 11 | 10-60% |
| Ultra-stable Y zeolite | 400-600 | 500 | 11 | 40-60% |
| NiW/zeolitic support | 400-600 | 500 | 11 | 60-75% |
| NiMo/zeolitic support | 350-550 | 500 | 2.2-11 | >90% |

Figure 5:
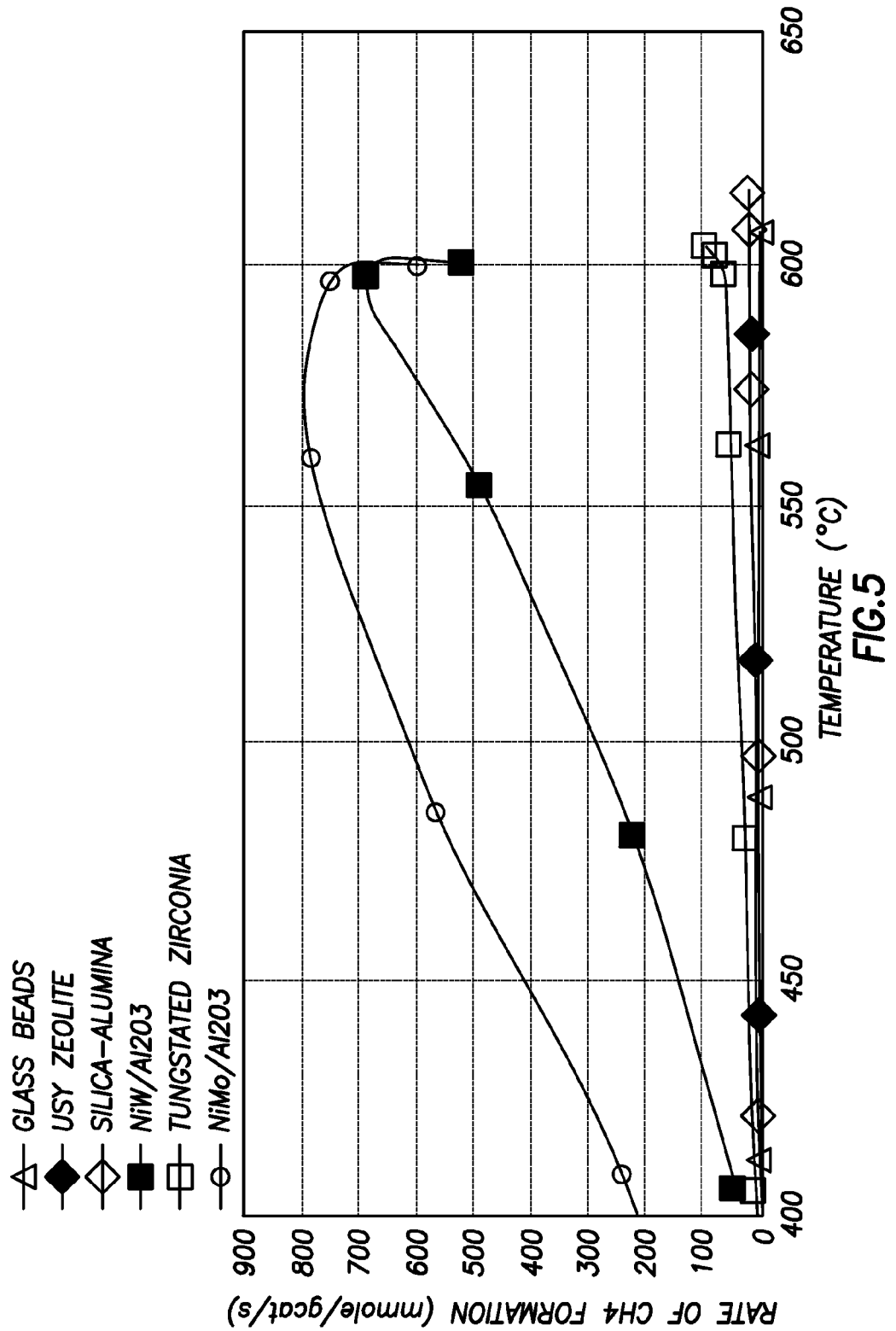
FIG. 5 depicts the rate of $CH_4$ formation at specified temperature ranges.
Figure 6:
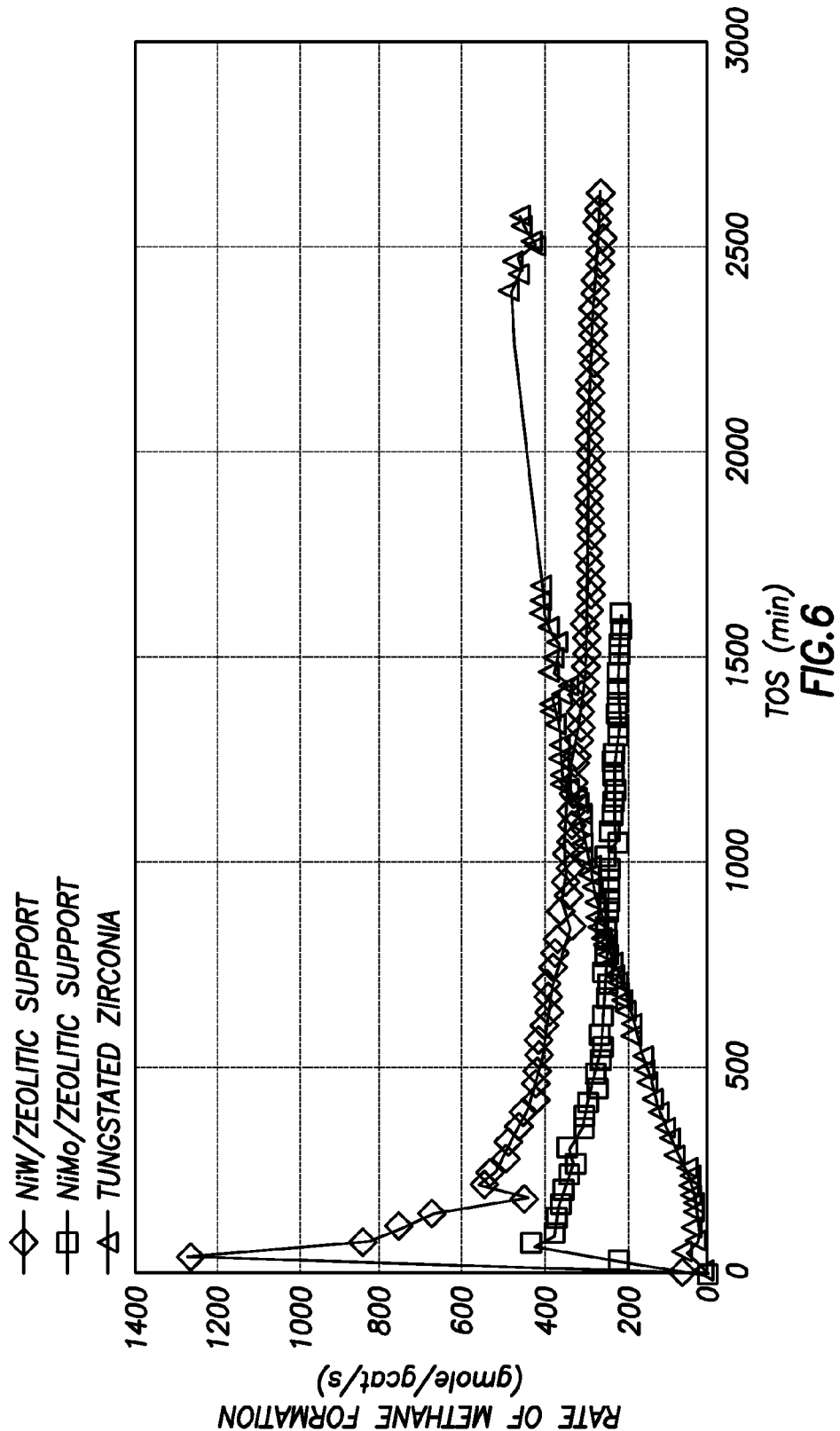
FIG. 6 depicts the rate of $CH_4$ formation for a specified period of time.

The ability for the catalysts to perform methanation is shown below and in FIG. 5 and FIG. 6. FIG. 5 demonstrates the rate of CH$_4$ formation at specified temperature ranges. FIG. 6 demonstrates the rate of CH$_4$ formation for a specified period of time.

| Catalyst | Temp. range ° C. | Pressure psig | WHSV h-1 | Rate of CH4 formation µmole/g cat/s |
| --- | --- | --- | --- | --- |
| Silica-alumina | 400-600 | 500 | 11 | <20 |
| Tungstated zirconia | 400-600 | 500 | 11 | 100-400 |
| Ultra-stable Y zeolite | 400-600 | 500 | 11 | <10 |
| NiW/zeolitic support | 400-600 | 500 | 11 | 300-700 |
| NiMo/zeolitic support | 350-550 | 500 | 2.2-11 | 150-800 |

The ability for the catalysts to perform water gas shift reactions is shown below.

| Catalyst | Temp. range ° C. | Pressure psig | WHSV h-1 | CO Conversion % |
| --- | --- | --- | --- | --- |
| Silica-alumina | 400-600 | 500 | 11 | <5% |
| Tungstated zirconia | 400-600 | 500 | 11 | 20% |
| Ultra-stable Y zeolite | 400-600 | 500 | 11 | <5% |
| NiW/zeolitic support | 400-600 | 500 | 11 | 30% |
| NiMo/zeolitic support | 350-550 | 500 | 2.2-11 | 30-50% |

The ability for the catalysts to perform sulfur removal is shown below.

| Catalyst | Temp. range ° C. | Pressure psig | WHSV h-1 | Sulfur uptake |
| --- | --- | --- | --- | --- |
| Silica-alumina | 400-600 | 500 | 11 | 0 |
| Tungstated zirconia | 400-600 | 500 | 11 | 3% |
| Ultra-stable Y zeolite | 400-600 | 500 | 11 | 0 |
| NiW/zeolitic support | 400-600 | 500 | 11 | <0.1% |
| NiMo/zeolitic support | 350-550 | 500 | 2.2-11 | <0.1% |

In closing, it should be noted that the discussion of any reference is not an admission that it is prior art to the present invention, especially any reference that may have a publication date after the priority date of this application. At the same time, each and every claim below is hereby incorporated into this detailed description or specification as additional embodiments of the present invention.

Although the systems and processes described herein have been described in detail, it should be understood that various changes, substitutions, and alterations can be made without departing from the spirit and scope of the invention as defined by the following claims. Those skilled in the art may be able to study the preferred embodiments and identify other ways to practice the invention that are not exactly as described herein. It is the intent of the inventors that variations and equivalents of the invention are within the scope of the claims while the description, abstract and drawings are not to be used to limit the scope of the invention. The invention is specifically intended to be as broad as the claims below and their equivalents.

The invention claimed is:
1. A process of:
producing a synthesis gas;
producing a treated synthesis gas by contacting the synthesis gas with a catalyst comprising:
(a) NiO;
(h) a metal mixture comprising of at least one of MoO$_3$ or WO$_3$;
(c) a mixture comprising at least one of: SiO$_2$ and Al$_2$O$_3$; and
(d) P$_2$O$_5$, and introducing the treated synthesis gas to a catalytic chemical reaction; wherein the synthesis gas is not heated prior to contact with the catalyst and the treated synthesis gas is not cooled prior to undergoing the catalytic chemical reaction, wherein the temperature range in which the synthesis gas is contacted with the catalyst is from 350° C. to 550° C.

2. The process of claim 1, wherein the NiO is present from 1 to 10 wt %.

3. The process of claim 1, wherein the metal mixture is present from 10 to 20 wt %.

4. The process of claim 1, wherein the $P_2O_5$ is present from 0.001 to 1 wt %.

5. The process of claim 1, wherein the metal sites on the catalyst are sulfided and the catalyst is capable of removing tar from a synthesis gas while performing methanation and water gas shift reactions at a temperature range from 300° C. to 600° C.

6. The process of claim 5, wherein the removal of tar is greater than 65% conversion at 350° C.

7. The process of claim 5, wherein the removal of tar is greater than 70% conversion at 400° C.

8. The process of claim 5, wherein the methanation produces from 150 to 800 μmol/g cat/s of $CH_4$.

9. The process of claim 5, wherein the water gas shift produces from 30 to 50% CO conversion.

10. The process of claim 1, wherein the catalytic chemical reaction is a Fischer-Tropsch, methanation or syngas to dimethyl ether to gasoline reaction.

11. A process of
producing a synthesis gas;
producing a treated synthesis gas by contacting the synthesis gas with a catalyst comprising:
(a) NiO present from 1 to 10 wt %;
(b) a metal mixture comprising of $MoO_3$ from 10 to 20 wt %;
(c) a mixture comprising at least one of: $SiO_2$ and $Al_2O_3$; and
(d) $P_2O_5$ from 0.001 to 1 wt %,
wherein the metal sites on the catalyst are sulfided and the catalyst is capable of removing tar, with greater than 65% conversion at 350° C., from an unheated synthesis gas while performing a methanation reaction, producing from 150 to 800 μmol/g cat/s of $CH_4$, and a water gas shift reaction, producing from 30 to 50% CO conversion, at a temperature range from 350° C. to 550° C.; and
introducing the treated synthesis gas to a catalytic chemical reaction;
wherein the synthesis gas is not heated prior to contact with the catalyst and the treated synthesis gas is not cooled prior to undergoing the catalytic chemical reaction.

* * * * *